United States Patent [19]

Yanagi et al.

[11] Patent Number: 4,472,190

[45] Date of Patent: Sep. 18, 1984

[54] N-SUBSTITUTED-TETRAHYDROISOPH-THALIMIDE DERIVATIVES

[75] Inventors: Mikio Yanagi, Okegawa; Osamu Yamada, Ageo; Fumio Futatsuya, Omiya; Atsuhiko Shida, Ageo, all of Japan

[73] Assignee: Nippon Kayaku Kabushiki Kaisha, Tokyo, Japan

[21] Appl. No.: 409,182

[22] Filed: Aug. 18, 1982

[30] Foreign Application Priority Data

Aug. 25, 1981 [JP] Japan ............................. 56-132146

[51] Int. Cl.$^3$ .................... A01N 43/00; C07D 307/88
[52] U.S. Cl. ........................................ 71/88; 549/303
[58] Field of Search ............................ 549/303; 71/88

[56] References Cited

U.S. PATENT DOCUMENTS 3,990,880 11/1976 Mumford ........................... 549/303
4,148,625 4/1979 Ivagase ............................. 549/240

FOREIGN PATENT DOCUMENTS 54-125652 9/1979 Japan .

*Primary Examiner*—Jane T. Fan
*Attorney, Agent, or Firm*—Henry C. Nields

[57] ABSTRACT

A new N-substituted tetrahydroisophthalimde derivative represented by the formula:

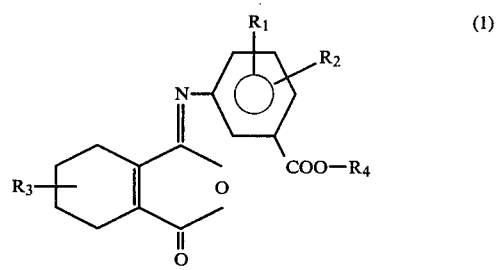

Wherein $R_1$ and $R_2$ are hydrogen or halogen, $R_3$ is hydrogen or lower alkyl and $R_4$ is alkyl which may be substituted by halogen or lower alkoxy, and preparation methods thereof and herbicidal composition comprising one or more of said derivatives as active ingredients, is disclosed.

18 Claims, No Drawings

N-SUBSTITUTED-TETRAHYDROISOPHTHALIMIDE DERIVATIVES

DETAILED DESCRIPTION OF THE INVENTION

The present invention relates to a new N-substituted tetrahydroisophthalimide derivative represented by the formula:

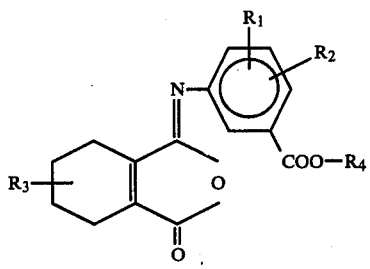

Wherein $R_1$ and $R_2$ are hydrogen or halogen, $R_3$ is hydrogen or lower alkyl and $R_4$ is alkyl which may be substituted by halogen or lower alkoxy, and preparation methods thereof and herbicidal composition comprising one or more of said derivatives as active ingredients.

It is disclosed in patents, for example, Japanese Patent Laid-open Nos. 23962/1978 and 125652/1979 that N-substituted tetrahydroisophthalimide derivatives have a herbicidal activity. The present inventors have found that a compound formed by introducing a carboxy derivative group in a meta position of the N-(substituted phenyl) derivatives unexpectedly shows a remarkably strong herbicidal activity as compared with the said known compounds and have completed the present invention.

As N-(substituted phenyl) tetrahydroisophthalimide introduced a carboxy derivative group, the following compounds are disclosed in Table 1 of Japanese Patent Laid-open No. 23962/1978.

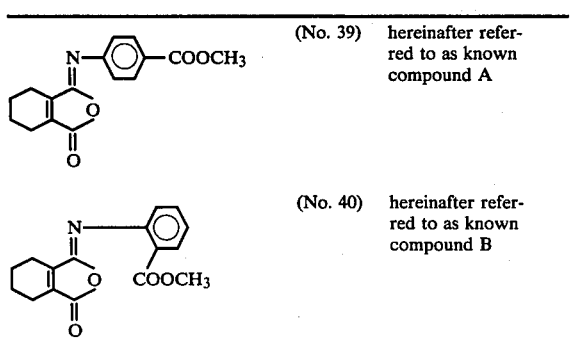

As a result of studies, the inventors have found the fact that the introduction of a carboxy derivative group into a meta position of the N-substituted phenyl group enhances the herbicidal activity remarkably. The degree of enhancement of the activity can not be easily expected from those of the known compound A or B having a methoxycarbonyl group in para or ortho position. Besides, the herbicidal activity is further enhanced by introducing another substituent in addition to the carboxyl derivative group in a meta position. Namely, a compound of the formula (1) wherein the carboxy derivative group is introduced into the meta position has a remarkably strong herbicidal activity. In a paddy field, it exhibits not only an excellent herbicidal effect in a low dosage against annual weeds such as barnyard grasses and broadleaf weeds, but also a strong effect on perennial weeds such as mizugayatsuri, bulrush, water chestnut, needle spikerush and arrowhead which are troublesome to control. In an up-land, the compound shows also a good herbicidal effect by both pre- and post-emergence treatments and it has been found to be extremely effective in a low dosage especially against broadleaf weeds belonging to Amaranthaceae, Chenopodiaceae and Polygonaceae. On the other hand, the compound is hardly phytotoxic to crops such as rice, wheat, oat, corn, soybean, cotton or sunflower and it has proved to be a herbicidal composition of practical use.

As the halogen in the compound of formula (1) of the present invention, there can be mentioned fluorine, chlorine and bromine. As the lower alkyls, there can be mentioned those having 1 to 4 carbon atoms such as methyl, ethyl, propyl and butyl. As the lower alkyls which may be substituted by halogen or lower alkoxy, there can be mentioned those having 1 to 8 carbon atoms such as methyl, ethyl, n-propyl, i-propyl, n-butyl, i-butyl, sec-butyl, tert-butyl, n-pentyl, i-pentyl, 1,1-dimethylpropyl, n-hexyl, 1-methylpentyl, 1,3-dimethylbutyl, 1-ethylbutyl, n-heptyl, 1-ethylpentyl, n-octyl, 1-ethylhexyl, 2-ethylhexyl, 2,2-dimethyl-4-methylpentyl, 2-chloroethyl, 2,2,2-trichloroethyl, 2-chloro-1-chloromethylethyl, 6-chloro-n-hexyl, 1-chloromethylethyl, 2-methoxyethyl, 2-ethoxyethyl, 2-methoxy-1-methylethyl, 2-butoxyethyl, 2-isopropoxyethyl and 2-(2'-methoxyethoxy)-ethyl.

A novel N-substituted tetrahydroisophthalimide derivative represented by formula (1) can be prepared, for example, by treating a compound represented by the following formula:

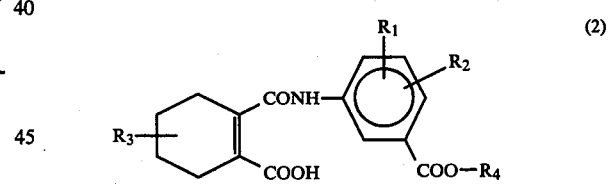

wherein $R_1$, $R_2$, $R_3$ and $R_4$ are the same as defined in the formula (1), with a dehydrating condensation agent in the presence of an inert solvent. This reaction is carried out at $-20°$ to $100°$ C., preferably $0°$ to $50°$ C., for about 30 minutes to 6 hours. As the dehydrating condensation agents, there are used carbodiimide derivatives such as dicyclohexylcarbodiimide and diethylcarbodiimide and also combination of a base and an acyl halogenating agent or an acylating agent. As the bases, there are used aliphatic, aromatic or heterocyclic tertiary bases such as triethylamine, dimethylaniline and pyridine, and alkali metal carbonates or bicarbonates such as sodium carbonate, potassium carbonate and sodium bicarbonate. As the acyl halogenating agents, there are used thionyl chloride and phosphorus oxychloride and as the acylating agents, there are used organic acid anhydrides and chlorocarbonate esters. As the inert solvent, there are used hydrocarbons such as toluene, xylene and hexane; halogenated hydrocarbons such as chloroform and chlorobenzene; ketones such as acetone and methyl ethyl ketone; ethers such as diethyl ether; dioxane; tetrahydrofuran and ethyl acetate.

A starting compound of the formula (2) can be prepared according to a known method (for example, a method according to Japanese Patent Laid-open No. 431/1974).

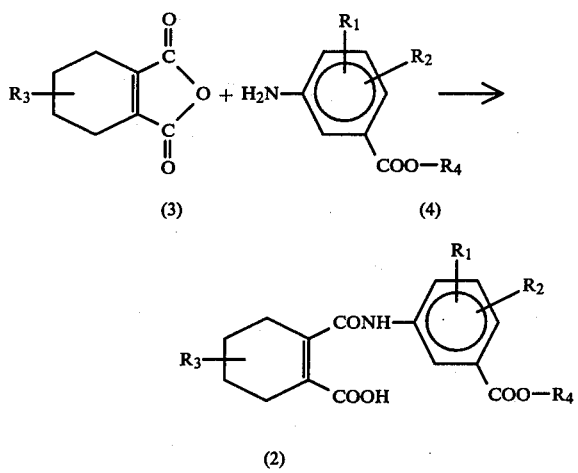

wherein $R_1$, $R_2$, $R_3$ and $R_4$ are the same as defined in the formula (1). Namely, the starting compound of formula (2) can be prepared by reacting a $\Delta^1$-tetrahydrophthalic anhydride of the formula (3) with a substantially equimolar amount of an amines of the formula (4) in an inert solvent at 10° to 100° C., preferably 20° to 60° C., for 5 minutes to 6 hours. As the inert solvents there can be used acetic acid and alcohols such as ethyl alcohol as well as the aforementioned solvents. The resulting compound of the formula (2) may be subjected, to dehydrating-cyclization reaction without isolation. As compounds of the present invention which show the preferred herbicidal activity, there can be mentioned those of the formula (1) wherein $R_1$ and $R_2$ are hydrogen or halogen, $R_3$ is hydrogen or lower alkyl and $R_4$ is chain alkyl having 1 to 8 carbon atoms which may be substituted by halogen or lower alkoxy.

More preferred compounds of the present invention are those of the formula (1) wherein $R_1$ and $R_2$ are hydrogen or halogen, $R_3$ is hydrogen or lower alkyl and $R_4$ is chain alkyl having 1 to 8 carbon atoms which may be substituted by lower alkoxy.

Moreover the compounds which exhibit most preferred herbicidal activity are those of the formula (1) wherein $R_1$ is Cl or Br, $R_2$ is hydrogen, Cl or F, $R_3$ is hydrogen or methyl and $R_4$ is chain alkyl having 2 to 4 carbon atoms. Examples of such compounds are compound Nos. 4, 5, 6, 8, 10, 11, 12, 13, 14, 16 and 17.

In the drawings, FIG. 1 shows an infrared absorption spectrum of compound No. 8 in potassium bromide, FIG. 2 shows that of compound No. 12, FIG. 3 shows that of compound No. 14 and FIG. 4 shows that of compound No. 17.

The detailed explanation will be given in the following examples.

SYNTHESIS EXAMPLE 1

N-(3-Methoxycarbonylphenyl)-$\Delta^1$-tetrahydroisophthalimide (Compound No. 1)

3.04 g (0.02 mol) of $\Delta^1$-tetrahydrophthalic anhydride was dissolved in 15 ml of acetone. To this solution was dropped slowly a solution of 3.17 g (0.021 mol) of methyl 3-amino-benzoate in 15 ml of acetone. The resulting solution was stirred at room temperature for 2 hours. The obtained crystals were filtered and washed with a small amount of acetone to obtain 5.5 g of N-(3-methoxy-carbonylphenyl)-$\Delta^1$-tetrahydrophthalamic acid, melting point 148°-150° C.

A mixture of 1.15 g of trifluoroacetic anhydride and 1.1 g of triethylamine was added at room temperature to a mixture of 1.51 g (0.005 mol) of the obtained crystals and 10 ml of dioxane. The solution was stirred for 30 minutes and then poured onto ice water. The product was extracted with ethyl acetate, concentrated and recrystallized from a benzene/n-hexane solvent mixture to obtain 1.1 g of crystals of the desired substance. Melting point: 120°-123° C.

Elementary analysis: $C_{16}H_{15}NO_4$; calculated: C: 67.36, H: 5.30, N: 4.91; found: C: 67.35, H: 5.39, N: 4.95.

SYNTHESIS EXAMPLE 2

N-(4-Chloro-3-isopropoxycarbonylphenyl)-$\Delta^1$-tetrahydroisophthalimide (Compound No. 5)

14.16 g (0.093 mol) of $\Delta^1$-tetrahydrophthalic anhydride was dissolved in 60 ml of benzene. To this solution was dropped slowly a solution of 21.37 g (0.10 mol) of isopropyl 5-amino-2-chlorobenzoate in 60 ml of benzene. The resulting solution was stirred for 4 hours at room temperature. The obtained crystals were filtered and washed with a small amount of benzene to obtain 29 g of N-(4-chloro-3-isopropoxycarbonylphenyl)-$\Delta^1$-tetrahydrophthalamic acid, melting point 133°-134° C.

27.22 g (0.0744 mol) of the obtained crystals was suspended in 200 ml of benzene. To the suspension was added 18.42 g (0.089 mol) of dicyclohexylcarbodiimide and the mixture was stirred for 2 hours at room temperature. Benzene-insoluble matter was filtered off and the filtrate was concentrated in vacuum. The obtained oily product was mixed with a small amount of n-hexane and left standing to precipitate crystals. The crystals were filtered and washed with a small amount of n-hexane to obtain 21.2 g of crystals. Melting point: 100°-102° C.

Elementary analysis: $C_{18}H_{18}ClNO_4$; calculated: C: 62.16, H: 5.21, N: 4.02; found: C: 62.35, H: 5.25, N: 3.98.

SYNTHESIS EXAMPLE 3

N-(4-Chloro-6-fluoro-3-isopropoxycarbonylphenyl)-$\Delta^1$-tetrahydroisophthalimide (Compound No. 13)

17.7 g (0.116 mol) of $\Delta^1$-tetrahydrophthalic anhydride was dissolved in 73 ml of benzene. To this solution was dropped slowly a solution of 28.85 g (0.124 mol) of isopropyl 5-amino-2-chloro-4-fluorobenzoate in 73 ml of benzene. The resulting solution was stirred for 4 hours at room temperature. The formed crystals were filtered and washed with a small amount of benzene to obtain 21 g of N-(4-chloro-6-fluoro-3-isopropoxycarbonyl-phenyl)-$\Delta^1$-tetrahydrophthalamic acid. Melting point: 91°-93° C.

20.15 g (0.0525 mol) of the obtained crystals was suspended in 140 ml of benzene. This solution was mixed with 13 g (0.0630 mol) of dicyclohexylcarbodiimide and then stirred for 2 hours at room temperature. Benzene-insoluble matter was filtered off and the filtrate was concentrated in vacuum. The obtained oily product was mixed with a small amount of n-hexane and left standing to precipitate crystals. The crystals were filtered and washed with a small amount of n-hexane to obtain 17 g of crystals. Melting point: 83°-86° C.

Elementary analysis: $C_{18}H_{17}FClNO_4$; calculated: C: 59.10, H: 4.69, N: 3.83; found: C: 59.35, H: 4.72, N: 3.90.

SYNTHESIS EXAMPLE 4

N-(4-Chloro-3-isopropoxycarbonylphenyl)-4(or 5)-methyl-$\Delta^1$-tetrahydroisophthalimide (Compound No. 8)

5.8 g (0.0307 mol) of 4-methyl-$\Delta^1$-tetrahydrophthalic anhydride was dissolved in 15 ml of tetrahydrofuran. To this solution was added slowly 5 g (0.0234 mol) of isopropyl 5-amino-2-chlorobenzoate. After the resulting solution was stirred for 1 hour at 45° C., it was cooled. The obtained crystals were filtered and washed with a small amount of ether to obtain 8.6 g of N-(4-chloro-3-isopropoxycarbonylphenyl)-4(or 5)-methyl-$\Delta^1$-tetrahydroisophthalamic acid. Melting point: 123°–124° C.

9.03 g (0.024 mol) of the obtained crystals was suspended in 60 ml of benzene. To the suspension was added 5.9 g (0.028 mol) of dicyclohexylcarbodiimide at room temperature and the temperature rose to 38° C. After that, the mixture was stirred for 2 hours at room temperature. Benzene-insoluble matter was filtered off and the filtrate was concentrated in vacuum. The obtained crystals were filtered and washed with a small amount of n-hexane to obtain 8.24 g of crystals. Melting point: 78°–80° C.

Elementary analysis: $C_{19}H_{20}ClNO_4$; calculated: C: 63.07, H: 5.57, N: 3.87; found: C: 63.09, H: 5.57, N: 3.88.

The infrared absorption spectrum of compound No. 8 in potassium bromide is shown in FIG. 1.

SYNTHESIS EXAMPLE 5

N-(4-Bromo-3-isopropoxycarbonylphenyl)-4(or 5)methyl-$\Delta^1$-tetrahydroisophthalimide (Compound No. 12)

3.12 g (0.018 mol) of 4-methyl-$\Delta^1$-tetrahydrophthalic anhydride was dissolved in 15 ml of ether. To this solution was added slowly 5 g (0.0187 mol) of isopropyl 5-amino-2-bromobenzoate. After the resulting solution was stirred for 3 hours at 36° C. and it was cooled. The formed crystals were filtered and washed with a small amount of ether to obtain 5.95 g of N-(4-bromo-3-isopropoxycarbonylphenyl)-4(or 5)methyl-$\Delta^1$-tetrahydrophthalamic acid. Melting point: 123°–125° C.

18.76 g (0.044 mol) of the obtained crystals was suspended in 120 ml of benzene. This solution was mixed with 10.9 g (0.053 mol) of dicyclohexylcarbodiimide and then stirred for 2 hours at room temperature. Benzene-insoluble matter was filtered off. The filtrate was concentrated in vacuum and was purified with silica gel column chromatography. The purified solution was concentrated in vacuum. The crystals were filtered and washed with a small amount of n-hexane to obtain 14.3 g of light-yellow crystals. Melting point: 73°–76° C.

Elementary analysis: $C_{19}H_{20}BrNO_4$; calculated: C: 56.17, H: 4.96, N: 3.45; found: C: 56.18, H: 4.95, N: 3.46.

The infrared absorption spectrum of compound No. 12 in potassium bromide is shown in FIG. 2.

SYNTHESIS EXAMPLE 6

N-(4,6-Dichloro-3-isopropoxycarbonylphenyl)-4(or 5)methyl-$\Delta^1$-tetrahydroisophthalimide (Compound No. 14)

3.32 g (0.02 mol) of 4-methyl-$\Delta^1$-tetrahydrophthalic anhydride was dissolved in 15 ml of ether. To this solution was added slowly 4.96 g (0.02 mol) of isopropyl 5-amino-2,4-dichlorobenzoate. After the resulting solution was stirred at 36° C. for 3 hours and it was cooled. The obtained crystals were filtered and washed with a small amount of ether to obtain 5.8 g of N-(4,6-dichloro-3-isopropoxycarbonylphenyl)-4(or 5)methyl-$\Delta^1$-tetrahydrophthalamic acid. Melting point: 114°–115° C.

2.5 g (0.0061 mol) of the obtained crystals was suspended in 15 ml of benzene. To the suspension was added 1.5 g (0.0073 mol) of dicyclohexylcarbodiimide and the mixture was stirred for 2 hours at room temperature. Benzene-insoluble matter was filtered off and the filtrate was concentrated in vacuum. The obtained crystals were washed with a small amount of n-hexane to obtain 2.05 g of light-yellow crystals. Melting point: 80°–81.5° C.

Elementary analysis: $C_{19}H_{19}Cl_2NO_4$; calculated: C: 57.59, H: 4.83, N: 3.54; found: C: 57.61, H: 4.82, N: 3.56.

The infrared absorption spectrum of compound No. 14 in potassium bromide is shown in FIG. 3.

SYNTHESIS EXAMPLE 7

N-(4-Chloro-6-fluoro-3-isopropoxycarbonylphenyl)-4(or 5)methyl-$\Delta^1$-tetrahydroisophthalimide (Compound No. 17)

11.35 g (0.068 mol) of 4-methyl-$\Delta^1$-tetrahydrophthalic anhydride was dissolved in 40 ml of benzene. To this solution was dropped slowly a solution of 17 g (0.073 mol) of isopropyl 5-amino-2-chloro-4-fluorobenzoate in 40 ml of benzene. The resulting solution was stirred for 5 hours at room temperature. The obtained crystals were filtered and washed with a small amount of hexane to obtain 18 g of N-(4-chloro-6-fluoro-3-isopropoxycarbonylphenyl)-4(or 5)-methyl-$\Delta^1$-tetrahydrophthalamic acid. Melting point: 110°–113° C.

14.95 g (0.038 mol) of the obtained crystals was suspended in 90 ml of benzene. To the suspension was added 9.3 g (0.045 mol) of dicyclohexylcarbodiimide and the mixture was stirred for 2 hours at room temperature. Benzene-insoluble matter was filtered off. The filtrate was concentrated in vacuum, was divided and was purified with silica gel column chromatography. The crystals were filtered and washed with a small amount of n-hexane to obtain 10.1 g of light-yellow crystals. Melting point: 72°–76° C.

Elementary analysis: $C_{19}H_{19}ClFNO_4$; calculated: C: 60.08, H: 5.04, N: 3.69; found: C: 60.12, H: 5.03, N: 3.71

The infrared absorption spectrum of compound No. 17 in potassium bromide is shown in FIG. 4.

The compounds of the following table were obtained according to the above method.

TABLE 1

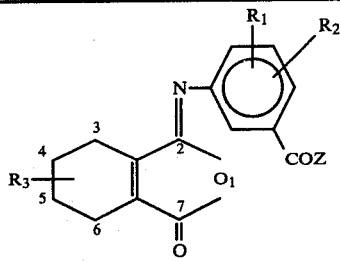

| Compound No. | $R_1$ | $R_2$ | $R_3$ | Z | m.p. (°C.), refractive index and/or FIG. No. of infrared absorption spectrum | Appearance |
|---|---|---|---|---|---|---|
| 1 | H | H | H | $OCH_3$ | 120–123 | light-yellow crystal |
| 2 | H | H | H | $OC_2H_5$ | 97–99 | white crystal |
| 3 | H | H | H | $OC_3H_7(i)$ | $n_D^{25}$ 1.5673 | light-yellow oil |
| 4 | 4-Cl | H | H | $OC_2H_5$ | 73–74 | light-yellow crystal |
| 5 | 4-Cl | H | H | $OC_3H_7(i)$ | 100–102 | light-yellow crystal |
| 6 | 4-Cl | H | H | $OC_4H_9(s)$ | 60–62 | light-yellow crystal |
| 7 | 4-Cl | H | H | $O-CH(CH_3)-CH_2-CH(CH_3)-CH_3$ | $n_D^{25}$ 1.5681 | light-yellow oil |
| 8 | 4-Cl | H | 4-$CH_3$ or 5-$CH_3$ | $OC_3H_7(i)$ | 78–80 FIG. 1 | light-yellow crystal |
| 9 | 4-Cl | 6-Cl | H | $OCH_3$ | 87–91 | light-yellow crystal |
| 10 | 4-Cl | 6-Cl | H | $OC_3H_7(i)$ | 72–77 | light-yellow crystal |
| 11 | 4-Br | H | H | $OC_3H_7(i)$ | 100–102 | light-yellow crystal |
| 12 | 4-Br | H | 4-$CH_3$ or 5-$CH_3$ | $OC_3H_7(i)$ | 73–76 FIG. 2 | light-yellow crystal |
| 13 | 4-Cl | 6-F | H | $OC_3H_7(i)$ | 83–86 | light-yellow crystal |
| 14 | 4-Cl | 6-Cl | 4-$CH_3$ or 5-$CH_3$ | $OC_3H_7(i)$ | 80–81.5 FIG. 3 | light-yellow crystal |
| 15 | 4-Cl | H | H | $OCH_2CH(C_2H_5)(CH_2)_3CH_3$ | $n_D^{25}$ 1.5634 | yellow oil |
| 16 | 4-Br | 6-F | H | $OC_3H_7(i)$ | 81–82 | light-yellow crystal |
| 17 | 4-Cl | H | 4-$CH_3$ or 5-$CH_3$ | $OC_3H_7(i)$ | 72–76 FIG. 4 | light-yellow crystal |
| 18 | 4-Cl | H | H | $O-CH(CH_2F)-CH_2F$ | 73–76 | light-yellow crystal |
| 19 | 4-Cl | H | H | $OCH_2CH_3OCH_3$ | $n_D^{25}$ 1.5918 | yellow oil |
| known compound A | | | | (structure: bicyclic with $-COOCH_3$) | 97–98 | |
| known compound B | | | | (structure: bicyclic with $COOCH_3$) | 109–111 | |

Note:
In compound Nos. 8, 12, 14 and 17, $R_3$ (methyl) is bonded at 4- or 5-position of tetrahydrobenzene ring.

The compounds of the present invention can be used either as it is or in the form of a formation according to The adjuvants mentioned above include carriers (diluents) and other adjuvants such as extending agents, emulsifiers, wetting agents, dispersing agents, fixing agents and disintegrators.

As the liquid carriers, there are used water, aromatic hydrocarbons such as toluene and xylene, alcohols such as methanol, butanol and glycols, ketones such as acetone, amides such as dimethylformamide, sulfoxides such as dimethyl sulfoxide, methylnaphthalene, cyclohexane, animal or vegetable oils, fatty acids and fatty acid esters.

As solid carriers, there are mentioned clay, kaolin, talc, diatomaceous earth, silica, calcium carbonate, montmorillonite, bentonite, feldspar, quartz, alumina, sawdust, or the like.

As the emulsifiers or the dispersing agents, surfactants are generally used. They include anionic, cationic, nonionic and amphoteric surfactants such as sodium salts of sulfated higher alcohol, stearyltrimethylammonium chloride, polyoxyethylene alkylphenyl ether and laurylbetaine.

Extending agents include lignin sulfonate and calcium caseinate, wetting agents include sodium alkylnaphthalene sulfonate and ammonium polyoxyethylenealkylphenylether sulfate, fixing agent include polyvinyl alcohol, polyvinyl acetate and carboxymethyl cellulose (CMC), and disintegrators include methyl cellulose and sodium salts of CMC.

Any type of said formulations not only can be used alone, but also may be mixed with fungicides, insecticides, plant growth regulators, acaricides, agriculture and horticulture fungicides, soil fungicides, soil conditioners or nematocides and further can be used in combination with fertilizers or other herbicides. The content of a compound (active ingredient) of the present invention in the formulations varies with types of formulation, methods of application and other conditions, but generally it is 0.1 to 95 weight %, preferably 0.2 to 50 wt %, and accordingly the content of adjuvants is 5 to 99.9 weight %, preferably 50 to 99.8 weight %. In detail a preferable range of the content is shown as under.

|  | Compound (Weight %) | Adjuvant (Weight %) |
| --- | --- | --- |
| Dusts | 0.2–20 | 80–99.8 |
| Emulsifiable concentrates | 1–80 | 20–99 |
| Wettable powders | 10–80 | 20–90 |
| Granules and micro granules | 0.2–20 | 80–99.8 |
| Flowable suspension concentrates | 1–80 | 20–99 |

In case of grass killing by use of the herbicidal composition of the present invention, a quantity of the formulation used is different with kinds of the active ingredient and sites of application, but generally it is within the range of 1 to 100 g, preferably 3 to 75 g, of the compound per are (100 m$^2$).

Detailed description will be made below with reference to Examples of formulations of the present invention, but the kind and mixing ratio of adjuvants are not limited to those in these examples and can vary within wider ranges. Parts are by weight.

FORMULATION EXAMPLE 1

Emulsifiable Concentrates 50 parts of Compound No. 7 was dissolved in 35 parts of a mixture (1:1) of xylene and methylnaphthalene and the solution was further mixed with 15 parts of a mixture (8:2) of polyoxyethylene alkylphenyl ether and calcium alkylbenzenesulfonate to obtain an emulsifiable concentrate.

FORMULATION EXAMPLE 2

Dusts 5 parts of Compound No. 13 was mixed with 95 parts of clay and pulverized to obtain a dust.

FORMULATION EXAMPLE 3

Wettable Powders 50 parts of Compound No. 5 was mixed with 10 parts of diatomaceous earth and 32 parts of kaolin, then uniformly blended with 8 parts of a mixture of sodium laurylsulfate and sodium 2,2'-dinaphthyl methanesulfonate, and finely pulverized to obtain a wettable powder.

FORMULATION EXAMPLE 4

Granules 5 parts of a fine powder of Compound No. 16 was coated on 94.5 parts of silica grains (16–32 mesh) by using a methanol solution of 0.5 part of polyvinyl acetate as a binding agent in a proper mixer to obtain a granule.

FORMULATION EXAMPLE 5

Flowable Suspension Concentrates 40 parts of a fine powder of Compound 17, 10 parts of ethylene-glycolmonobutylether, 10 parts of a surfactant (mixture of trioxyalkylether, polyoxyethylenenonylphenylether and sodium alkylarylsulfonate), 3 parts of colloidal aluminium silicate hydrate and 22 parts of water are uniformly mixed and further blended under stirring in a homomixer for 20 minutes to obtain a flowable suspension concentrate.

The excellent heribicidal activity of the compound (active ingredient) of the present invention will be illustrated in the following examples. Each test was carried out on a 2-replication system and the test results are given in the average value.

TEST EXAMPLE 1

Pre-emergence Treatment Under a Flooded Condition

A given amount of paddy field soil was filled in each Wagner pot sized 1/5,000 are to provide a condition similar to that of a paddy field and there were sown a given amount of seeds of barnyard grass, monochoria, toothcup, false pimpernel, water-wort and umbrella plant. In addition, tubes of arrowhead were buried 1 cm under the surface of soil at the rate of 3 pieces per pot and the pot was flooded with water 3 cm deep. Then, the pot was applied dropwise with a diluted solution of the compound of the present invention at a rate of 6.25 to 50 g of the compound of the present invention per are. After three days, 3 pieces of rice seedlings (variety: Nihonbare) in 2.5-leaf stage were transplanted to each pot. Thirty days after the treatment, the herbicidal activity and the phytotoxicity against paddy rice were observed. The test results were classified on the following index as shown in TABLE 2.

Herbicidal activity index:
5: complete weeding
4: up to about 80% weeding
3: up to about 60% weeding
2: up to about 40% weeding
1: up to about 20% weeding 0: no effect
Phytotoxicity index:
— no damage
+ slight damage
++ some damage
+++ moderate damage
++++ heavy damage
× complete death

TABLE 2

Test Example 1
Pre-emergence treatment under a flooded condition

| Compound No. | Dosage g/are | Herbicidal activity | | | | Phytotoxicity against paddy rice |
|---|---|---|---|---|---|---|
| | | Barnyard grass | Broad leaf (1) | Umbrella sedge (2) | Arrow head | |
| 1 | 50 | 3 | 5 | 5 | 3 | — |
| | 25 | 2 | 5 | 5 | 2.5 | — |
| | 12.5 | 1 | 5 | 5 | 2 | — |
| 2 | 25 | 3 | 5 | 5 | 2.5 | — |
| | 12.5 | 2.5 | 5 | 5 | 2 | — |
| | 6.25 | 2 | 5 | 5 | 2 | — |
| 3 | 25 | 3 | 5 | 5 | 2 | — |
| | 12.5 | 2 | 5 | 5 | 2 | — |
| | 6.25 | 2 | 5 | 5 | 1 | — |
| 4 | 25 | 5 | 5 | 5 | 5 | + |
| | 12.5 | 5 | 5 | 5 | 5 | ± |
| | 6.25 | 5 | 5 | 5 | 2 | — |
| 5 | 25 | 5 | 5 | 5 | 3 | — |
| | 12.5 | 5 | 5 | 5 | 2 | — |
| | 6.25 | 5 | 5 | 5 | 2 | — |
| 6 | 25 | 5 | 5 | 5 | 3 | — |
| | 12.5 | 5 | 5 | 5 | 2 | — |
| | 6.25 | 5 | 5 | 5 | 1 | — |
| 7 | 25 | 5 | 5 | 5 | 4.5 | ± |
| | 12.5 | 5 | 5 | 5 | 4 | — |
| | 6.25 | 5 | 5 | 5 | 2 | — |
| 8 | 25 | 5 | 5 | 5 | 5 | + |
| | 12.5 | 5 | 5 | 5 | 5 | — |
| | 6.25 | 5 | 5 | 5 | 5 | — |
| 9 | 25 | 5 | 5 | 5 | 5 | ++ |
| | 12.5 | 5 | 5 | 5 | 5 | + |
| | 6.25 | 2 | 5 | 5 | 2.5 | — |
| 10 | 25 | 5 | 5 | 5 | 5 | ++ |
| | 12.5 | 5 | 5 | 5 | 5 | ± |
| | 6.25 | 5 | 5 | 5 | 5 | ± |
| 11 | 25 | 5 | 5 | 5 | 5 | — |
| | 12.5 | 5 | 5 | 5 | 4 | — |
| | 6.25 | 5 | 5 | 5 | 2 | — |
| 12 | 25 | 5 | 5 | 5 | 4 | — |
| | 12.5 | 5 | 5 | 5 | 3 | — |
| | 6.5 | 5 | 5 | 5 | 2 | — |
| 13 | 25 | 5 | 5 | 5 | 5 | + |
| | 12.5 | 5 | 5 | 5 | 5 | ± |
| | 6.25 | 5 | 5 | 5 | 5 | ± |
| 14 | 25 | 5 | 5 | 5 | 5 | + |
| | 12.5 | 5 | 5 | 5 | 5 | ± |
| | 6.5 | 5 | 5 | 5 | 4 | — |
| 16 | 25 | 5 | 5 | 5 | 5 | ± |
| | 12.5 | 5 | 5 | 5 | 5 | — |
| | 6.5 | 5 | 5 | 5 | 5 | — |
| 17 | 25 | 5 | 5 | 5 | 5 | + |
| | 12.5 | 5 | 5 | 5 | 5 | ± |
| | 6.5 | 5 | 5 | 5 | 5 | — |
| 18 | 25 | 4.5 | 5 | 5 | 4.5 | — |
| | 12.5 | 4 | 5 | 5 | 3 | — |
| 19 | 25 | 4.8 | 5 | 5 | 5 | + |
| | 12.5 | 4.5 | 5 | 5 | 5 | ± |
| known compound A | 25 | 0 | 5 | 4 | 0 | — |
| | 12.5 | 0 | 5 | 3 | 0 | — |
| | 6.25 | 0 | 0 | 0 | 0 | — |
| known compound B | 50 | 0 | 0 | 0 | 0 | — |
| | 25 | 0 | 0 | 0 | 0 | — |

TABLE 2-continued

Test Example 1
Pre-emergence treatment under a
flooded condition

| Compound No. | Dosage g/are | Barnyard grass | Broad leaf (1) | Umbrella sedge (2) | Arrow head | Phytotoxicity against paddy rice |
|---|---|---|---|---|---|---|
| standard compound C | 25 | 3 | 4 | 3 | 0 | + |
|  | 12.5 | 1 | 2 | 0 | 0 | − |

Remarks:
(1) Broad leaf: monochoria, toothcup, false pimpernel, water-wort
(2) Umbrella sedge: umbrella plant Known compound A

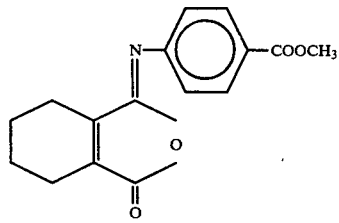

Known compound B

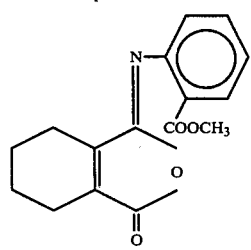

Standard compound C

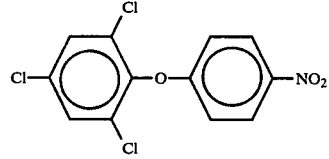

TEST EXAMPLE 2

Post-emergence Treatment Under a Flooded Condition

A given amount of paddy field soil was filled in each Wagner pot sized 1/5,000 are to provide a condition similar to that of a paddy field and there were sown a given amount of seeds of barnyard grass, monochoria, toothcup, false pimpernel, water-wort and umbrella plant. In addition, tubers of arrowhead were buried 1 cm under the surface of soil at the rate of 3 pieces per pot, the pot was flooded with water 3 cm deep and then placed in a greenhouse. When the weeds grew to reach 2- to 3-leaf stage, a diluted solution of the compound of the present invention was applied to the flood at a rate of 12.5 to 50 g of the compound of the present invention per are.

After 30 days from the treatment with the diluted solution, the herbicidal activity was observed and the results are shown in TABLE 3. The classification index of the results is the same as in Test Example 1.

TABLE 3

Test Example 2
Post-emergence treatment under a
flooded condition

| Compound No. | Dosage g/are | Barnyard grass | Broad leaf (1) | Umbrella sedge (2) | Arrow head |
|---|---|---|---|---|---|
| 1 | 25 | 3 | 5 | 5 | 3 |
|  | 12.5 | 2 | 5 | 5 | 2 |
| 2 | 25 | 3 | 5 | 5 | 3 |
|  | 12.5 | 2 | 5 | 5 | 2 |
| 3 | 25 | 2 | 5 | 5 | 2 |
|  | 12.5 | 1 | 5 | 5 | 1 |
| 4 | 50 | 5 | 5 | 5 | 5 |
|  | 25 | 3 | 5 | 5 | 5 |
| 5 | 25 | 5 | 5 | 5 | 4 |
|  | 12.5 | 5 | 5 | 5 | 2 |
| 6 | 25 | 5 | 5 | 5 | 3 |
|  | 12.5 | 4 | 5 | 5 | 2 |
| 7 | 50 | 2 | 5 | 5 | 2 |
|  | 25 | 2 | 5 | 5 | 1 |
| 8 | 25 | 5 | 5 | 5 | 5 |
|  | 12.5 | 5 | 5 | 5 | 5 |
| 9 | 50 | 5 | 5 | 5 | 5 |
|  | 25 | 4 | 5 | 5 | 5 |
| 10 | 50 | 5 | 5 | 5 | 3 |
|  | 25 | 5 | 5 | 5 | 2 |
| 11 | 50 | 4 | 5 | 5 | 3 |
|  | 25 | 3 | 5 | 5 | 2 |
| 12 | 25 | 4.5 | 5 | 5 | 4 |
|  | 12.5 | 4 | 5 | 5 | 3 |
| 13 | 25 | 5 | 5 | 5 | 5 |

TABLE 3-continued

Test Example 2
Post-emergence treatment under a flooded condition

| Compound No. | Dosage g/are | Barnyard grass | Broad leaf (1) | Umbrella sedge (2) | Arrow head |
|---|---|---|---|---|---|
| | 12.5 | 5 | 5 | 5 | 5 |
| 14 | 50 | 5 | 5 | 5 | 4.5 |
| | 25 | 5 | 5 | 5 | 3.5 |
| 16 | 50 | 5 | 5 | 5 | 5 |
| | 25 | 5 | 5 | 5 | 5 |
| 17 | 25 | 5 | 5 | 5 | 5 |
| | 12.5 | 5 | 5 | 5 | 5 |
| known compound A | 50 | 0 | 0 | 0 | 0 |
| | 25 | 0 | 0 | 0 | 0 |
| known compound B | 50 | 0 | 0 | 0 | 0 |
| | 25 | 0 | 0 | 0 | 0 |
| standard compound C | 50 | 1 | 1 | 0 | 0 |
| | 25 | 0 | 0 | 0 | 0 |

Remarks:
(1) } the same as in Test Example 1
(2) }
known compounds A and B } the same as in Test Example 1
standard compound C }

TEST EXAMPLE 3

Test on Perennial Weeds in a Paddy Field

A given amount of paddy field soil was filled in a Wagner pot sized 1/5,000 are to provide a condition similar to that of a paddy field and there was sown a given amount of seeds of bulrush. In addition, tubers of mizugayatsuri and water chestnut were buried 3 cm under the surface of soil at the rate of 3 pieces per pot and then the pot was flooded with water 3 cm deep. The pre-emergence treatment was conducted on the second day after seeds and tubers of the weeds were put into soil, while the post-emergence treatment was effected at 2-leaf stage of bulrush, 2- to 3-leaf stage of mizugayatsuri or when water chestnut grew 5 to 6 cm high by applying a diluted solution of the compound of the present invention to the respective floods at a rate of 6.25 to 50 g of the compound of the present invention per are.

The herbicidal activity was respectively observed on 30th day after the treatment and the test results are shown in TABLE 4. The results is classified in the same index as in Test Example 1.

As seen in the results of Test Examples 1, 2 and 3, the compounds of the present invention showed a remarkable herbicidal effect against the principal annual and perennial weeds in paddy fields in pre- and post-emergence treatment. Furthermore, it was found that the compound of the present invention showed only little phytotoxicity in pre- and post-transplantation treatment.

Then, the Test Examples in field are shown below.

TEST EXAMPLE 4

A given amount of field soil was filled in a round plastic case 8 cm across and 8 cm deep, and a given

TABLE 4

Test Example 3
Test on perennial weeds in paddy field

| Compound No. | Dosage g/are | Pre-emergence treatment | | | Post-emergence treatment | | |
|---|---|---|---|---|---|---|---|
| | | Bulrush | Mizugayatsuri | Water chestnut | Bulrush | Mizugayatsuri | Water chestnut |
| 1 | 50 | 5 | 4 | 3 | 5 | 3.5 | 3 |
| | 25 | 4 | 3 | 2 | 3 | 3 | 2 |
| | 12.5 | 3 | 2 | 1 | 2 | 2 | 1 |
| 3 | 50 | 5 | 5 | 4 | 5 | 5 | 3 |
| | 25 | 4 | 4 | 3 | 3 | 3 | 2 |
| | 12.5 | 3 | 3 | 2 | 2 | 2 | 1 |
| 5 | 25 | 5 | 5 | 5 | 5 | 5 | 5 |
| | 12.5 | 5 | 4.5 | 4.5 | 5 | 4 | 4 |
| | 6.25 | 5 | 4 | 3 | 5 | 3 | 3 |
| 8 | 50 | 5 | 5 | 5 | 5 | 5 | 5 |
| | 25 | 5 | 5 | 5 | 5 | 5 | 5 |
| | 12.5 | 5 | 5 | 5 | 5 | 5 | 4 |
| 13 | 50 | 5 | 5 | 5 | 5 | 5 | 5 |
| | 25 | 5 | 5 | 5 | 5 | 5 | 5 |
| | 12.5 | 5 | 5 | 5 | 5 | 5 | 4 |
| 17 | 25 | 5 | 5 | 5 | 5 | 5 | 5 |
| | 12.5 | 5 | 5 | 5 | 5 | 5 | 5 |
| | 6.25 | 5 | 5 | 5 | 5 | 5 | 4 |
| known compound A | 25 | 0 | 0 | 0 | 0 | 0 | 0 |
| | 12.5 | 0 | 0 | 0 | 0 | 0 | 0 |
| | 6.25 | 0 | 0 | 0 | 0 | 0 | 0 |
| known compound B | 25 | 0 | 0 | 0 | 0 | 0 | 0 |
| | 12.5 | 0 | 0 | 0 | 0 | 0 | 0 |
| | 6.25 | 0 | 0 | 0 | 0 | 0 | 0 |
| standard compound C | 50 | 2 | 0 | 0 | 0 | 0 | 0 |
| | 25 | 1 | 0 | 0 | 0 | 0 | 0 |
| | 12.5 | 0 | 0 | 0 | 0 | 0 | 0 | amount of seeds of crabgrass, foxtail, pigweed, and lamb's-quarters were sown there and covered with soil 0.5 to 1 cm thick. Immediately thereafter, a diluted formulation solution containing the compound of the present invention was applied to treat the whole surfaces of soil in the case at a rate of 12.5 to 25 g of active ingredient per are. After the treatment the cultivation was done in a greenhouse and the herbicidal activity was observed on the 20th day. The test was carried out on a 2-replication system and each average value was sought. The results is classified in the same index as in Test Example 1. The test results are shown in TABLE 5.

powder diluted with water containing the compound of the present invention was sprayed on the body of plants at the rate of 12.5, 25 or 50 g of active ingredient per are.

The test was conducted on a 2-replication system. Twenty days after treatment the test results were observed on the same index as in Test Example 1 and the results are shown in TABLE 6.

TABLE 6

Test Example 5
Post-emergence treatment on weeds

| Compound No. | Dosage g/are | Herbicidal effect foxtail | Herbicidal effect pigweed | Compound No. | Dosage g/a | Herbicidal effect foxtail | Herbicidal effect pigweed |
|---|---|---|---|---|---|---|---|
| 1 | 50 | 3 | 5 | 11 | 50 | 3 | 5 |
|   | 25 | 2 | 5 |    | 25 | 3 | 5 |
|   | 12.5 | 1 | 5 |  | 12.5 | 2 | 5 |
| 2 | 50 | 3 | 5 | 12 | 50 | 3 | 5 |
|   | 25 | 2 | 5 |    | 25 | 2 | 5 |
|   | 12.5 | 1 | 5 |  | 12.5 | 1 | 5 |
| 3 | 50 | 2.5 | 5 | 13 | 50 | 5 | 5 |
|   | 25 | 2 | 5 |    | 25 | 5 | 5 |
|   | 12.5 | 1 | 5 |  | 12.5 | 5 | 5 |
| 4 | 50 | 3 | 5 | 14 | 50 | 4 | 5 |
|   | 25 | 2 | 5 |    | 25 | 3 | 5 |
|   | 12.5 | 1 | 5 |  | 12.5 | 2 | 5 |
| 5 | 50 | 4 | 5 | 15 | 50 | 5 | 5 |
|   | 25 | 3 | 5 |    | 25 | 5 | 5 |
|   | 12.5 | 2 | 5 |  | 12.5 | 5 | 5 |
| 6 | 50 | 3.5 | 5 | 16 | 50 | 5 | 5 |
|   | 25 | 3 | 5 |    | 25 | 5 | 5 |
|   | 12.5 | 2 | 5 |  | 12.5 | 5 | 5 |
| 7 | 50 | 5 | 5 | 18 | 50 | 5 | 5 |
|   | 25 | 4 | 5 |    | 25 | 5 | 5 |
|   | 12.5 | 3 | 5 |  | 12.5 | 5 | 5 |
| 8 | 50 | 5 | 5 | known compound A | 50 | 0 | 0 |
|   | 25 | 5 | 5 |   | 25 | 0 | 0 |
|   | 12.5 | 5 | 5 |  | 12.5 | 0 | 0 |
| 9 | 50 | 3 | 5 | known compound B | 50 | 0 | 0 |
|   | 25 | 2 | 5 |   | 25 | 0 | 0 |
|   | 12.5 | 1 | 5 |  | 12.5 | 0 | 0 |
| 10 | 50 | 4 | 5 | standard compound C | 50 | 2.5 | 4 |
|   | 25 | 3.5 | 5 |   | 25 | 2 | 3 |
|   | 12.5 | 3 | 5 |  | 12.5 | 0 | 1 |

TABLE 5

Test Example 4
Pre-emergence soil surface treatment on weeds

| Compound No. | Dosage g/are | Herbicidal activity foxtail | crabgrass | pigweed | buckwheat |
|---|---|---|---|---|---|
| 3 | 25 | 3 | 3 | 3 | 4 |
|   | 12.5 | 2 | 2 | 2 | 3 |
| 5 | 25 | 3 | 5 | 5 | 5 |
|   | 12.5 | 2 | 4 | 5 | 5 |
| 7 | 25 | 4 | 5 | 5 | 5 |
|   | 12.5 | 3 | 3 | 5 | 5 |
| 8 | 25 | 5 | 5 | 5 | 5 |
|   | 12.5 | 5 | 5 | 5 | 5 |
| 10 | 25 | 5 | 5 | 5 | 5 |
|   | 12.5 | 5 | 5 | 5 | 5 |
| 11 | 25 | 4 | 4 | 5 | 5 |
|   | 12.5 | 3 | 3 | 5 | 5 |
| 12 | 25 | 2 | 3 | 5 | 5 |
|   | 12.5 | 1 | 2 | 5 | 5 |
| 13 | 25 | 5 | 5 | 5 | 5 |
|   | 12.5 | 5 | 5 | 5 | 5 |
| 16 | 25 | 5 | 5 | 5 | 5 |
|   | 12.5 | 5 | 5 | 5 | 5 |
| known compound A | 25 | 0 | 0 | 0 | 0 |
|   | 12.5 | 0 | 0 | 0 | 0 |
| known compound B | 25 | 0 | 0 | 0 | 0 |
|   | 12.5 | 0 | 0 | 0 | 0 |
| standard compound C | 25 | 2 | 4 | 3 | 2 |
|   | 12.5 | 1 | 2 | 1 | 0 |

TEST EXAMPLE 5

A given amount of field soil was filled in a round plastic case 8 cm across and 8 cm deep, and a given amount of seeds of foxtail and pigweed were sown. When they grew up to 3- to 4-leaf stage, a wettable

TEST EXAMPLE 6

A given amount of field soil was filled in a plastic vessel sized 23 cm × 4.5 × 12.5 cm and a given amount of seeds of soybean, cotton, corn, wheat, sunflower and rice were sown there and covered with soil about 3 cm thick. Immediately thereafter, a diluted formulation solution containing the compound of the present invention was sprayed on the soil surface using a small sprayer at the rate of 25 or 50 g of active ingredient per respective vessels. After the treatment the crops were grown in a greenhouse and 20 days later the degree of phytotoxicity against each crop was observed. The test was carried out on a 2-replication system and each average value was sought.

The results is classified in the same index as in Test Example 1 and results are shown in TABLE 7.

TABLE 7

Test Example 6
Phytotoxicity against crops

| Compound No. | Dosage g/are | soybean | cotton | corn | wheat | rice | sunflower |
|---|---|---|---|---|---|---|---|
| 3 | 50 | — | — | — | — | — | — |
|   | 25 | — | — | — | — | — | — |
| 5 | 50 | — | — | — | — | — | — |
|   | 25 | — | — | — | — | — | — |
| 7 | 50 | — | — | — | — | — | — |
|   | 25 | — | — | — | — | — | — |
| 8 | 50 | — | — | — | — | — | — |

TABLE 7-continued

| Compound No. | Dosage g/are | Test Example 6 Phytotoxicity against crops | | | | | |
|---|---|---|---|---|---|---|---|
| | | soybean | cotton | corn | wheat | rice | sunflower |
| 10 | 25 | — | — | — | — | — | — |
| | 50 | — | — | — | — | — | — |
| 11 | 25 | — | — | — | — | — | — |
| | 50 | — | — | — | — | — | — |
| 12 | 25 | — | — | — | — | — | — |
| | 50 | — | — | — | — | — | — |
| 13 | 25 | — | — | — | — | — | — |
| | 50 | — | — | — | — | — | — |
| 16 | 25 | — | — | — | — | — | — |
| | 50 | — | — | — | — | — | — |
| 17 | 25 | — | — | — | — | — | — |
| | 50 | — | — | — | — | — | — |
| 18 | 25 | — | — | — | — | — | — |
| | 50 | — | — | — | — | — | — |
| 19 | 25 | — | — | — | — | — | — |
| | 50 | — | — | — | — | — | — |
| known compound A | 25 | — | — | — | — | — | — |
| | 50 | — | — | — | — | — | — |
| known compound B | 25 | — | — | — | — | — | — |
| | 50 | — | — | — | — | — | — |
| standard compound C | 25 | ++ | + | + | ++ | + | ++ |
| | 50 | +++ | ++ | ++ | +++ | ++ | +++ |

As obvious from the results of Test Examples 4 and 5, the compound of the present invention has proved to exhibit a very good herbicidal activity both in pre-emergence and post-emergence treatments of main weeds in the field. On the other hand, it is clear from the results of Test Example 6 that the compound of the present invention has no phytotoxicity against crops and is a herbicide suitable for use in farmlands.

What is claimed is:

1. An N-substituted-tetrahydroisophthalimide derivative represented by the formula:

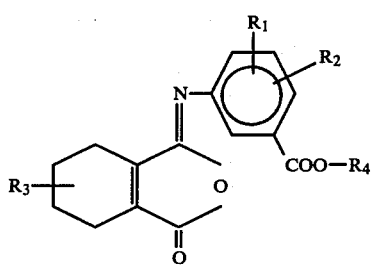

wherein $R_1$ and $R_2$ are hydrogen or halogen, $R_3$ is hydrogen or lower alkyl and $R_4$ is alkyl having 1 to 8 carbon atoms which may be substituted by halogen or lower alkoxy.

2. The N-substituted-tetrahydroisophthalimide derivative according to claim 1 wherein $R_1$ and $R_2$ are hydrogen or halogen, $R_3$ is hydrogen or lower alkyl and $R_4$ is chain alkyl having 1 to 8 carbon atoms which may be substituted by lower alkoxy.

3. The N-substituted-tetrahydroisophthalimide derivative according to claim 1 wherein $R_1$ is Cl or Br, $R_2$ is hydrogen, Cl or F, $R_3$ is hydrogen or methyl and $R_4$ is chain alkyl having 2 to 4 carbon atoms.

4. The compound of claim 3 which is N-(4-chloro-3-ethoxycarbonylphenyl) $\Delta^1$-tetrahydroisophthalimide.

5. The compound of claim 3 which is N-(4-chloro-3-isopropoxycarbonylphenyl) $\Delta^1$-tetrahydroisophthalimide.

6. The compound of claim 3 which is N-(4-chloro-3-sec-butoxycarbonylphenyl) $\Delta^1$-tetrahydroisophthalimide.

7. The compound of claim 3 which is represented by the formula:

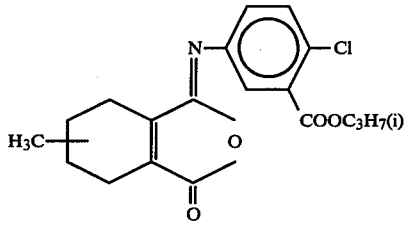

wherein methyl is bonded at 4- or 5-position of tetrahydrobenzene ring.

8. The compound of claim 3 which is N-(4,6-dichloro-3-isopropoxycarbonylphenyl) $\Delta^1$-tetrahydroisophthalimide.

9. The compound of claim 3 which is N-(4-bromo-3-isopropoxycarbonylphenyl) $\Delta^1$-tetrahydroisophthalimide.

10. The compound of claim 3 which is represented by the formula:

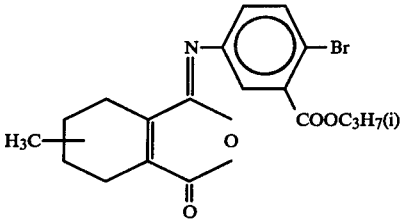

wherein methyl is bonded at 4- or 5-position of tetrahydrobenzene ring.

11. The compound of claim 3 which is N-(4-chloro-6-fluoro-3-isopropoxycarbonylphenyl) $\Delta^1$-tetrahydroisophthalimide.

12. The compound of claim 3 which is represented by the formula:

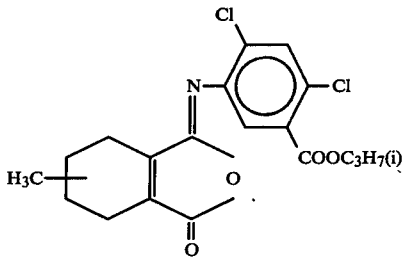

wherein methyl is bonded at 4- or 5-position of tetrahydrobenzene ring.

13. The compound of claim 3 which is N-(4-bromo-6-fluoro-3-isopropoxycarbonylphenyl) $\Delta^1$-tetrahydroisophthalimide.

14. The compound of claim 3 which is represented by the formula:

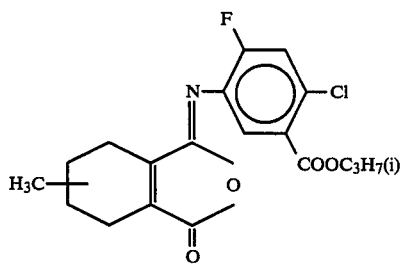

wherein methyl is bonded at 4- or 5-position of tetrahydrobenzene ring.

15. A herbicidal composition comprising an effective herbicidal amount of an N-substituted-tetrahydroisophthalimide derivative as an active ingredient, represented by the formula:

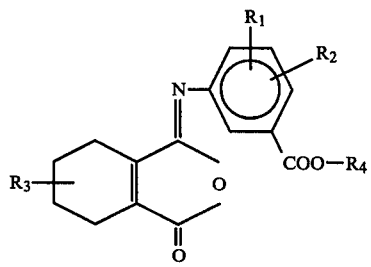

wherein $R_1$ and $R_2$ are hydrogen or halogen, $R_3$ is hydrogen or lower alkyl and $R_4$ is alkyl having 1 to 8 carbon atoms which may be substituted by hydrogen or lower alkoxy and adjuvants.

16. A herbicidal composition according to claim 15 comprising 0.1 to 95% by weight of an N-substituted-tetrahydroisophthalimide derivative as an active ingredient as claimed in claim 1 and 5 to 99.9% by weight of adjuvants.

17. The herbicidal composition according to claim 15 comprising N-substituted-tetrahydroisophthalimide derivative as an active ingredient, represented by the formula (1) wherein $R_1$ and $R_2$ are hydrogen or halogen, $R_3$ is hydrogen or lower alkyl and $R_4$ is chain alkyl having 1 to 8 carbon atoms which may be substituted by lower alkoxy.

18. The herbicidal composition according to claim 15 comprising N-substituted-tetrahyaroisophthalimide derivative as an active ingredient, represented by the formula (1) wherein $R_1$ is Cl or Br, $R_2$ is hydrogen, Cl or F, $R_3$ is hydrogen or methyl and $R_4$ is chain alkyl having 2 to 4 carbon atoms.

* * * * *